US009718056B2

(12) United States Patent
Cadle-Davidson

(10) Patent No.: US 9,718,056 B2
(45) Date of Patent: Aug. 1, 2017

(54) MICROFLUIDICS POLYMERASE CHAIN REACTION AND HIGH RESOLUTION MELT DETECTION

(71) Applicant: Molly M. Cadle-Davidson, Geneva, NY (US)

(72) Inventor: Molly M. Cadle-Davidson, Geneva, NY (US)

(73) Assignee: Syracuse University, Syracuse, NY (US)

( * ) Notice: Subject to any disclaimer, the term of this patent is extended or adjusted under 35 U.S.C. 154(b) by 544 days.

(21) Appl. No.: 14/215,864

(22) Filed: Mar. 17, 2014

(65) Prior Publication Data

US 2014/0287420 A1 Sep. 25, 2014

Related U.S. Application Data

(60) Provisional application No. 61/799,165, filed on Mar. 15, 2013.

(51) Int. Cl.
*C12Q 1/68* (2006.01)
*B01L 3/00* (2006.01)
*B01L 7/00* (2006.01)

(52) U.S. Cl.
CPC ......... *B01L 3/502715* (2013.01); *B01L 7/525* (2013.01); *B01L 2300/0645* (2013.01); *B01L 2300/088* (2013.01); *B01L 2300/0816* (2013.01); *B01L 2300/0864* (2013.01); *B01L 2400/0487* (2013.01)

(58) Field of Classification Search
None
See application file for complete search history.

(56) References Cited

U.S. PATENT DOCUMENTS

| | | | | |
|---|---|---|---|---|
| 7,838,235 | B2 | 11/2010 | Caplin | |
| 7,857,957 | B2 | 12/2010 | Cheng | |
| 7,915,030 | B2 | 3/2011 | Inoue | |
| 2009/0042280 | A1 | 2/2009 | Yang | |
| 2009/0098540 | A1 | 4/2009 | Baeumner | |
| 2009/0143233 | A1 | 6/2009 | Knight | |
| 2009/0281250 | A1 | 11/2009 | DeSimone | |
| 2011/0104688 | A1 * | 5/2011 | Sundberg | B01L 3/50273 435/6.12 |
| 2011/0262316 | A1 | 10/2011 | Inoue | |

(Continued)

FOREIGN PATENT DOCUMENTS

| | | |
|---|---|---|
| WO | 2006085948 | 8/2006 |
| WO | 2009003184 | 12/2008 |

OTHER PUBLICATIONS

Vossen et al. (Human Mutation 2009, 30(6):860-866).*

(Continued)

*Primary Examiner* — Stephanie K Mummert

(74) *Attorney, Agent, or Firm* — Bond Schoeneck & King, PLLC; Frederick Price; George McGuire

(57) ABSTRACT

The present invention relates to a method and system for Polymerase Chain Reaction ("PCR"), High Resolution Melt ("HRM") analysis and microfluidics, and, more specifically, to a method and system for implementing the processes of PCR and HRM on a microscale in a microfluidics chamber for certain purposes including for purposes of DNA detection and/or extraction.

7 Claims, 1 Drawing Sheet

(56) References Cited

U.S. PATENT DOCUMENTS

2012/0058571 A1 3/2012 Knight
2015/0069045 A1* 3/2015 Coursey ............ B01L 3/502715
219/494

OTHER PUBLICATIONS

Rouleau et al. (Human Mutation 2009, 30:867-875).*
Chen et al. "Total Nucleic Acid Analysis Integrated on Microfluidic Devices" Lab on a Chip. 2007, 7, pp. 1413-1423.
Cho et al. "Recent Advances in Microfluidic Technologies for Biochemistry and Molecular Biology" BMB Rep., 2011, 44, pp. 705-712.
Erickson et al. "Integrated Microfluidic Devices" Analytica Chimica Acta., 2004, 507, pp. 11-26.
Fang et al. "Real-time PCR Microfluidic Devices with Concurrent Electrochemical Detection" Biosensors and Bioelectronics, 2009, 24, pp. 2131-2126.
Levon et al. "Potentiometric Monitoring DNA Hybridization" Biosensors and Bioelectronics, 2009, 24, pp. 3275-3280.
Levon et al. "Potentiometric Monitoring DNA Hybridization with Polyaniline/Nylon-6 Working Electrode" Polymer Science Series A, 2009, 51, pp. 701-707.
Liu et al. "Self-Contained, Fully Integrated Biochip for Sample Preparation, Polymerase Chain Reaction, Amplification, and DNA Microarray Detection" Anal. Chem., 2004, 76, pp. 1824-1831.
Park et al. "Advances in Microfluidic PCR for Point-of-Care Infectious Disease Diagnostics" Biotechnology Advances, 2011, 29, pp. 830-839.
Yamanaka et al. "Rapid Detection for Primary Screening of Influenza A Virus: Microfluidic RT-PCR chip and electrochemical DNA sensor" Analyst, 2011, 135, pp. 2064-2068.
Yueng et al. "Electrochemistry-Based Real-Time PCR on a Microchip" Anal. Chem., 2008, 80, pp. 363-368.
Zhang et al. "PCR Microfluidic Devices for DNA Amplification" Biotechnology Advances, 2006, 24, pp. 234-284.

* cited by examiner

Microfluidics (DNA extraction) PCR and HRM
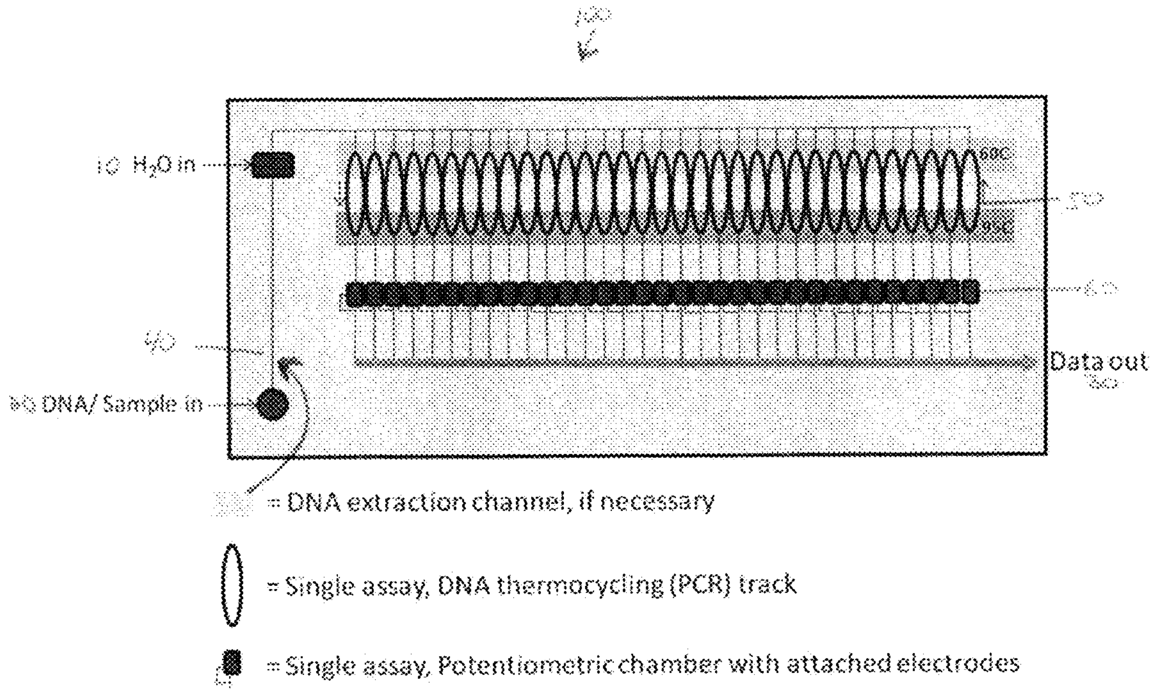

MICROFLUIDICS POLYMERASE CHAIN REACTION AND HIGH RESOLUTION MELT DETECTION

RELATED APPLICATION DATA

The present application claims the benefit of U.S. provisional patent application Ser. No. 61/799,165, filed Mar. 15, 2013, and is hereby incorporated by reference in its entirety.

BACKGROUND OF THE INVENTION

1. Field of the Invention

The present invention relates to a method and system for Polymerase Chain Reaction ("PCR"), High Resolution Melt ("HRM") analysis and microfluidics, and, more specifically, to a method and system for implementing the processes of PCR and HRM on a microscale in a microfluidics chamber for certain purposes including for purposes of DNA detection and/or extraction.

2. Description of the Related Art

Polymerase Chain Reaction ("PCR") is a ubiquitous molecular biology tool used in thousands of different applications. In brief, this molecular biology tool is used to produce ("amplify") a sufficient number (sometimes millions to billions) of copies of a particular DNA sequence so that the sequence can adequately be used in these applications. Essentially, PCR makes a sample of DNA that is large enough so that the sample can be appropriately analyzed. As just one example of a typical application for PCR amplification, it is a common detection and/or identification method and tool used, for example, in clinical applications, scientific investigations, and in biological warfare agent ("BWA") detection systems.

High Resolution Melt ("HRM") is another molecular biology tool. This tool is used to detect a variety of differences (e.g., mutations, other types of genetic sequence differences) in samples of double stranded DNA, which is based on the detected melting temperature/behavior of the double stranded DNA sequence(s) at issue. HRM is performed post PCR amplification, which is performed to obtain a sufficient number of copies of the DNA sequence(s) of interest.

The concept of doing PCR "on a chip" or using microfluidics is not fieldable by conventional technology at this time because no rugged detection system exists, most being based on fluorescence and optics.

BRIEF SUMMARY OF THE INVENTION

It is therefore a principal object and advantage of the present invention to provide a microfluidics-based PCR and HRM method and system that eliminates/alleviates one or more of the problems/issues with conventional related technologies.

It is a further object and advantage of the present invention to provide a microfluidics-based PCR and HRM method and system that addresses the need of a fieldable PCR that can be detected without the need of a fluorescent dye, expensive/fragile light source, or an optics system for detection.

Another object and advantage of the present invention is to provide a microfluidics-based PCR and HRM method and system that combines the processes necessary for amplification of DNA (PCR) and HRM and their subsequent detection into a single, fieldable device. The device can be small, lightweight, and have a rugged design for which no use of fluorescence and optics is required.

Another object and advantage of the present invention is to provide a microfluidics-based PCR and HRM method and system that combines the use of microfluidics for PCR with direct detection of DNA products (including detection of DNA based on its charge properties). The improvements gained by an embodiment of the present invention include, but are not limited to: 1. The combination of these two processes on a single "chip"; 2. Direct detection of DNA hybridization dynamics on a "chip".

In accordance with the following objects and advantages, an embodiment of the present invention provides a microfluidics-based PCR and HRM method and system that provides a "closed track" where PCR could take place, e.g., one oval-like track per assay. When cycling finished, a portion of the total amplicon is sent to a potentiometric monitoring chamber that is preloaded with a polyaniline layer, for example, and allowed to adsorb (or pre-loaded w/reference DNA, and blocked w/thiol groups), then another portion of the amplicon is sent to the chamber and allowed to anneal, change in voltage measured, denature w/temp increase and measure change in voltage→interpreted as melt curve→ID.

The details of one or more embodiments are described below and in the accompanying drawings. Other objects and advantages of the present invention will in part be obvious, and in part appear hereinafter.

BRIEF DESCRIPTION OF THE DRAWING(S)

The present invention will be more fully understood and appreciated by reading the following Detailed Description in conjunction with the accompanying drawings, in which:

FIG. 1 a schematic representation of an embodiment of the method and system according to the present invention.

DETAILED DESCRIPTION OF THE INVENTION

In accordance with an embodiment of the present invention, a goal is to provide a system and a method configured to detect insertions/deletions/polymorphisms larger than single base pairs. Probes can be larger than 6-75 bases. Detection of hybridization can be over a temperature change not a constant temperature. Further, as discussed herein, a system of an embodiment of the present invention can be implemented on a micro scale in a microfluidics chamber.

Referring now to the drawings, wherein like reference numerals refer to like parts throughout, there is seen in FIG. 1 a schematic representation of an embodiment of the method and system according to the present invention. FIG. 1 shows a micro-scaled microfluidics-based PCR and HRM system 100 (in which PCR followed by HRM take place) which can include, but is not limited to, an H2O input port 10, a DNA/Sample input port 20, a data output 30, a DNA extraction channel 40, a single assay, DNA thermocycling (PCR) track 50, and a single assay, potentiometric chamber with attached electrodes 60.

Advantages of the invention are illustrated by the Examples set forth herein. However, the particular conditions and details are to be interpreted to apply broadly in the art and should not be construed to unduly restrict or limit the invention in any way.

EXAMPLE

This Example describes a use of the micro-scaled microfluidics-based PCR and HRM system 100. Reaction components are preloaded into specific assay chambers. At the time of use, user-supplied DNA is injected via an onboard pump (not shown) into all chambers and the subsequent PCR reactions carried out by pumping the reactions back and forth across a temperature gradient from approximately 60 C to 95 C for a given number of cycles. After cycling and a final exposure to 95 C, the reactions are pumped into an HRM chamber preloaded with an electrode polymer, a single-stranded reference DNA (being the same length as the PCR product), and "empty" spaces in the electrode being blocked with thiol groups. These chambers are rapidly cooled from 95 C to 55 C and the concomitant ionic changes detected by the electrode and transmitted to onboard data collection.

In an alternative format, after the final exposure to about 95 C following cycling, the DNA is cooled to about 55 C and then pumped into the HRM chamber preloaded with the aforementioned reagents. The chambers are then rapidly heated from about 55 C to 95 C and the concomitant ionic changes detected by the electrode and transmitted to onboard data collection. These data are interpreted as melt/hybridization curves which are specific to the sequence of the DNA being interrogated and can be used to assign an identity/origin to the original DNA. A data collection device/module (not shown) programmed, configured, and/or structured to collect data and a data interpretation module programmed, configured, and/or structured to perform data interpretation are also contemplated. The detection of hybridization (a potentially melting too) can be accomplished by potentlometiic monitoring, for example, using a polyanhllnelNylon-6 electrode.

In another embodiment of the micro-scaled microfluidics-based PCR and HRM system 100, sample material such as plant, animal (including Human), or microbial tissue/cells is applied to a "Sample In" input port 20 (see FIG. 1). DNA is extracted by a combination of mechanical shearing of cells while the tissue passes through a microfluidic chamber and exposure to DNA extraction chemicals pumped into the extraction chamber. On board-extracted DNA is diluted as needed and injected into reaction chambers as described in the preceding paragraph.

In accordance with another embodiment of the present invention, one or more of the following is provided: DNA is put into system at top arrow, and quantified by UV at first port, diluted to a user controlled concentration; sample split between fluid channels: 1 channel per assay control(s); Per assay, reagent entry port, lyophylized deposition, microencapsulated reagents or some other means of delivering PCR reagents; microfluidic chambers carry (pressurized system) reaction through parallel channels leading to PCR temp conditions; 1 switchback per cycle; UV may be used to quantify DNA at low temp end of microfluidic channels; After m cycles, reaction moves through parallel melt channels that move more slowly between low and high temp a single time; a unique aspect includes the UV detection of DNA quantity at the low temp side of the platform and electro/chemical/magnetic detection of the melt during the last melt channels: Detection by one of the following: 1. loss of whole molecule energy as melt progresses (may be measured as the increased energy required to maintain temperature across gradient); 2. increase/change in magnetic field as melt progresses; 3. charge detection along microfluidic channels that is transmitted to data-out (rate and magnitude).

As will be appreciated by one skilled in the art, aspects of the present invention (including aspects of the data collection device and data interpretation module) may be embodied/implemented as a computer system, method or computer program product. The computer program product can have a computer processor or neural network, for example, that carries out the instructions of a computer program. Accordingly, aspects of the present invention may take the form of an entirely hardware embodiment, an entirely software embodiment or an embodiment combining software and hardware aspects that may all generally be referred to herein as a "circuit," "module" or "system." A module, as discussed herein, can include, among other things, the identification of specific functionality represented by specific computer software code of a software program. A software program may contain code representing one or more modules, and the code representing a particular module can be represented by consecutive or non-consecutive lines of code. Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The data collection device and data interpretation module can be connected with each other and/or to the micro-scaled microfluidics-based PCR and HRM system 100 to facilitate the transmission of information between them by a wired connection or any suitable wired or wireless network capable of transmitting communication, including but not limited to a telephone network, Internet, Intranet, local area network, Ethernet, online communication, offline communications, wireless communications and/or similar communications means.

Although the present invention has been described in connection with a preferred embodiment, it should be understood that modifications, alterations, and additions can be made to the invention without departing from the scope of the invention as defined by the claims.

What is claimed is:

1. A microfluidics-based polymerase chain reaction ("PCR") and high resolution melt ("HRM") system comprising a microfluidics chip comprising:

a PCR chamber configured to perform a PCR amplification on a DNA target sample, wherein the PCR chamber further comprises at least one closed single assay track and a pump configured to move the DNA target sample back and forth across a temperature gradient within the closed track between a first end of the closed track and a second end of the closed track for a predetermined number of amplification cycles; and a HRM chamber configured to perform a HRM analysis on the amplified DNA target.

2. The system of claim 1, wherein said at least one single assay track is oval-shaped.

3. The system of claim 1, wherein said temperature gradient is between about 55° C. and 95° C.

4. The system of claim 3, wherein the HRM chamber is configured to provide a HRM chamber temperature from between about 55° C. and 95° C.

5. The system of claim 1, wherein said HRM chamber further comprises a potentiometric monitoring chamber with attached electrodes configured to measure voltage changes and/or ionic changes obtained during the HRM analysis of the amplified DNA target and to transmit data obtained from the measurements of the voltage changes and/or ionic changes.

6. The system of claim 5, further comprising a data collection module programmed, configured, and/or structured to receive the voltage changes and/or ionic changes data transmitted from said HRM chamber.

7. The system of claim 6, wherein said data collection module is further programmed, configured, and/or structured to identify, characterize, and/or determine the origin of the DNA target sample based on the voltage changes and/or ionic changes data transmitted from said HRM chamber.

* * * * *